(12) United States Patent
Crews et al.

(10) Patent No.: US 11,304,770 B2
(45) Date of Patent: Apr. 19, 2022

(54) FORCE TRANSMISSION MECHANISM FOR SURGICAL INSTRUMENT, AND RELATED DEVICES, SYSTEMS, AND METHODS

(71) Applicant: INTUITIVE SURGICAL OPERATIONS, INC., Sunnyvale, CA (US)

(72) Inventors: Samuel T. Crews, Palomar Park, CA (US); Harsukhdeep Singh Ratia, Foster City, CA (US); Nicole Kernbaum, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 405 days.

(21) Appl. No.: 16/083,150

(22) PCT Filed: Mar. 8, 2017

(86) PCT No.: PCT/US2017/021284
§ 371 (c)(1),
(2) Date: Sep. 7, 2018

(87) PCT Pub. No.: WO2017/156070
PCT Pub. Date: Sep. 14, 2017

(65) Prior Publication Data
US 2019/0069967 A1 Mar. 7, 2019

Related U.S. Application Data

(60) Provisional application No. 62/305,867, filed on Mar. 9, 2016.

(51) Int. Cl.
*A61B 34/00* (2016.01)
*A61B 34/35* (2016.01)
*A61B 17/128* (2006.01)
*A61B 17/29* (2006.01)
*A61B 17/00* (2006.01)
*A61B 34/30* (2016.01)

(52) U.S. Cl.
CPC .......... *A61B 34/71* (2016.02); *A61B 17/1285* (2013.01); *A61B 17/29* (2013.01);
(Continued)

(58) Field of Classification Search
CPC .............. A61B 34/71; A61B 2034/715; A61B 2017/2944; A61B 2017/2936;
(Continued)

(56) References Cited

U.S. PATENT DOCUMENTS 6,394,998 B1   5/2002   Wallace et al.
6,817,974 B2   11/2004  Cooper et al.
(Continued)

FOREIGN PATENT DOCUMENTS

WO   WO-2015122944 A1   8/2015

OTHER PUBLICATIONS

International Search Report and Written Opinion for Application No. PCT/US2017/021284, dated Jul. 11, 2017, 17 pages.
(Continued)

*Primary Examiner* — Majid Jamialahmadi
(74) *Attorney, Agent, or Firm* — Jones Robb, PLLC

(57) ABSTRACT

A force transmission mechanism for a teleoperated surgical instrument includes a drive pulley, a drive cable operably coupled with the drive pulley, a driven pulley operably coupled with the drive cable, and an actuation member operably coupled to the driven pulley. The actuation member is configured to transmit force to actuate an end effector of the surgical instrument. Rotational motion of the driven pulley causes translational movement of the actuation element to actuate the end effector. Methods relate to operating a force transmission mechanism.

21 Claims, 6 Drawing Sheets

(52) U.S. Cl.
CPC .... *A61B 34/35* (2016.02); *A61B 2017/00398* (2013.01); *A61B 2017/2936* (2013.01); *A61B 2017/2944* (2013.01); *A61B 2034/301* (2016.02)

(58) Field of Classification Search
CPC .... A61B 2017/2932; A61B 2017/2912; A61B 34/30; A61B 34/37; A61B 34/32; A61B 2034/301; A61B 2034/302; A61B 2034/303; A61B 2034/304; A61B 2034/305
See application file for complete search history.

(56) References Cited

U.S. PATENT DOCUMENTS

| | | |
|---|---|---|
| 7,316,681 B2 | 1/2008 | Madhani et al. |
| 8,545,515 B2 | 10/2013 | Prisco et al. |
| 10,076,348 B2 | 9/2018 | Anderson et al. |
| 2007/0142969 A1* | 6/2007 | Devengenzo .......... G16H 40/63 700/245 |
| 2008/0119870 A1 | 5/2008 | Williams et al. |
| 2008/0125794 A1* | 5/2008 | Brock .................... A61B 34/30 606/130 |
| 2008/0196533 A1 | 8/2008 | Bergamasco et al. |
| 2012/0330287 A1 | 12/2012 | Yim |
| 2014/0249545 A1* | 9/2014 | Hyodo .................... A61B 34/30 606/130 |
| 2014/0338477 A1 | 11/2014 | Donlon et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

PROXIMAL ←——→ DISTAL

FORCE TRANSMISSION MECHANISM FOR SURGICAL INSTRUMENT, AND RELATED DEVICES, SYSTEMS, AND METHODS

RELATED APPLICATIONS

This patent application is a U.S. national stage application under 35 U.S.C. § 371(c) of International Application No. PCT/US2017/021284, which claims priority to and the benefit of the filing date of U.S. Provisional Patent Application 62/305,867, entitled "FORCE TRANSMISSION MECHANISM FOR SURGICAL INSTRUMENT, AND RELATED DEVICES, SYSTEMS, AND METHODS" filed Mar. 9, 2016, each of which is incorporated by reference herein in its entirety.

TECHNICAL FIELD

Aspects of the present disclosure relate to a surgical instrument force transmission mechanism, configured to impart rotation and translational movement to an actuation mechanism coupled to an end effector of the surgical instrument push/pull rod.

INTRODUCTION

Benefits of minimally invasive surgery are well known, and they include less patient trauma, less blood loss, and faster recovery times when compared to traditional, open incision surgery. In addition, the use of teleoperated, computer-assisted surgical systems (e.g., robotic systems that provide telepresence), such as the da Vinci® Surgical System commercialized by Intuitive Surgical, Inc. of Sunnyvale, Calif., is known. Such teleoperated surgical systems allow a surgeon to operate with intuitive control and increased precision when compared to manual minimally invasive surgeries.

Teleoperated surgical systems include one or more surgical instruments or tools. To perform actions directed by a surgeon, the teleoperated surgical system uses connections that permit motion of a surgical instrument, or a component on which a surgical instrument is mounted, in more than one direction. In other words, the connection may be used to provide more than one degree of freedom for the motion of a surgical instrument. Further, the connection may be used to translate motive force from an actuator to the medical instrument or to a component to which the instrument is mounted. Thus, a connection may be required to provide different functions and movements, even if these functions and movements may otherwise conflict with one another from a mechanical or structural sense.

SUMMARY

Exemplary embodiments of the present disclosure solve one or more of the above-mentioned problems and/or demonstrate one or more of the above-mentioned desirable features. Other features and/or advantages may become apparent from the description that follows.

In accordance with at least one exemplary embodiment, a force transmission mechanism for a teleoperated surgical instrument includes a drive pulley, a drive cable operably coupled with the drive pulley, a driven pulley operably coupled with the drive cable, and an actuation member operably coupled to the driven pulley. The actuation member is configured to transmit force to actuate an end effector of the surgical instrument. Rotational motion of the driven pulley causes translational movement of the actuation element to actuate the end effector.

In accordance with at least one exemplary embodiment, a surgical instrument for a teleoperated surgical system includes a shaft, an end effector disposed at a distal portion of the shaft, and a force transmission mechanism disposed at a proximal portion of the shaft. The force transmission mechanism includes a drive pulley, a drive cable operably coupled with the drive pulley, a driven pulley operably coupled with the drive cable, and an actuation member operably coupled to the driven pulley. The actuation member is configured to transmit force to actuate an end effector of the surgical instrument. Rotational motion of the driven pulley causes translational movement of the actuation element to actuate the end effector.

In accordance with at least one exemplary embodiment, a method of operating a surgical instrument includes winding a portion of a drive cable over a drive pulley by rotating the drive pulley responsive to a torque applied to the drive pulley, rotating a driven pulley by unwinding another portion of the drive cable from the driven pulley responsive to winding the portion of the drive cable over the drive pulley, translating an actuation element responsive to rotating the driven pulley, and operating an end effector of the surgical instrument responsive to translating the actuation element.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims. The claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Various exemplary embodiments herein may be implemented using a da Vinci® Surgical System (specifically, a Model IS4000, marketed as the da Vinci Xi® Surgical System), commercialized by Intuitive Surgical, Inc. of Sunnyvale, Calif. Persons of ordinary skill in the art will understand, however, that inventive aspects disclosed herein may be embodied and implemented in various ways, including computer-assisted teleoperated and manual embodiments and implementations. Implementations on da Vinci® Surgical Systems are merely exemplary and are not to be considered as limiting the scope of the inventive aspects disclosed herein.

Various exemplary embodiments of the present disclosure contemplate a remotely-controllable surgical instrument having a force transmission mechanism configured to convert input rotary motion to a translational movement of a push/pull rod, cable, or other actuation element. Exemplary embodiments of the present disclosure also contemplate such a force transmission mechanism for a teleoperated surgical instrument.

Figure 1:
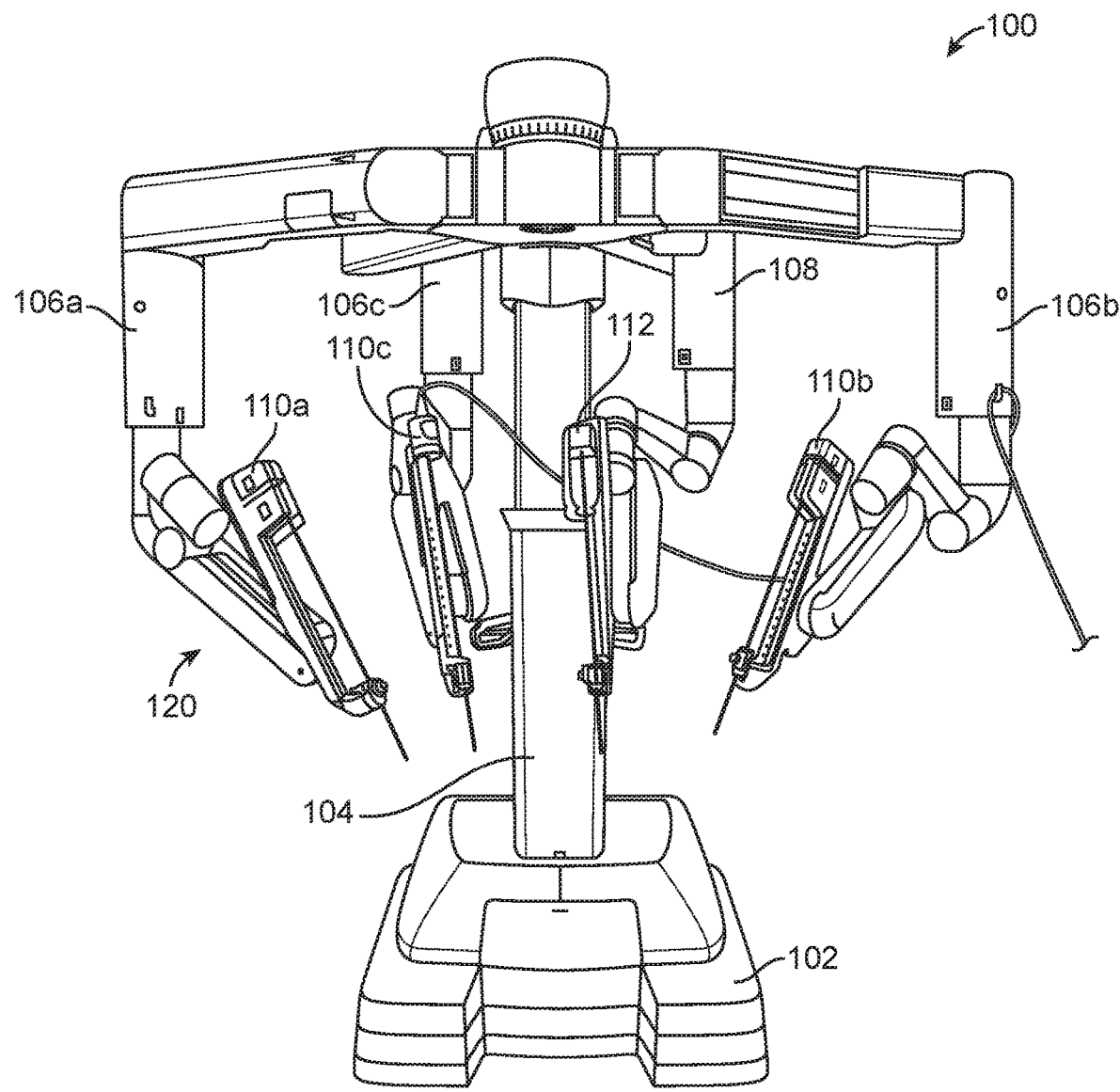
FIG. 1 is a front view of an exemplary embodiment of a patient side cart of a teleoperated surgical system.

FIG. 1 is a front view of the patient side cart 100 of a teleoperated surgical system. A teleoperated surgical system allows diagnostic and corrective surgical procedures to be performed on a patient. Such a teleoperated surgical system is described in U.S. Pat. No. 8,545,515 (filed Nov. 13, 2009), which is hereby incorporated by reference in its entirety. The patient side cart includes a base 102 that rests on the floor, a support tower 104 that is mounted on the base 102, and several arms that support surgical tools (which can include a stereoscopic endoscope). According to an exemplary embodiment, surgical tools may be arranged according to the embodiments described in U.S. Pat. No. 6,394,998 (filed Sep. 17, 1999) and U.S. Pat. No. 6,817,974 (filed Jun. 28, 2002), which are hereby incorporated by reference in their entirety.

As shown in FIG. 1, arms 106a, 106b are instrument arms that support and move the surgical instruments used to manipulate tissue, and arm 108 is a camera arm that supports and moves the endoscope. FIG. 1 also shows an optional third instrument arm 106c. FIG. 1 further shows interchangeable surgical instruments 110a, 110b, 110c mounted on the instrument arms 106a, 106b, 106c, and an endoscope 112 mounted on the camera arm 108, which may be interchangeable with a surgical instrument. A surgical instrument 110a may be mounted to an arm 106a via a patient-side manipulator ("PSM") portion 120 that supports and moves the surgical instrument.

Figure 2:
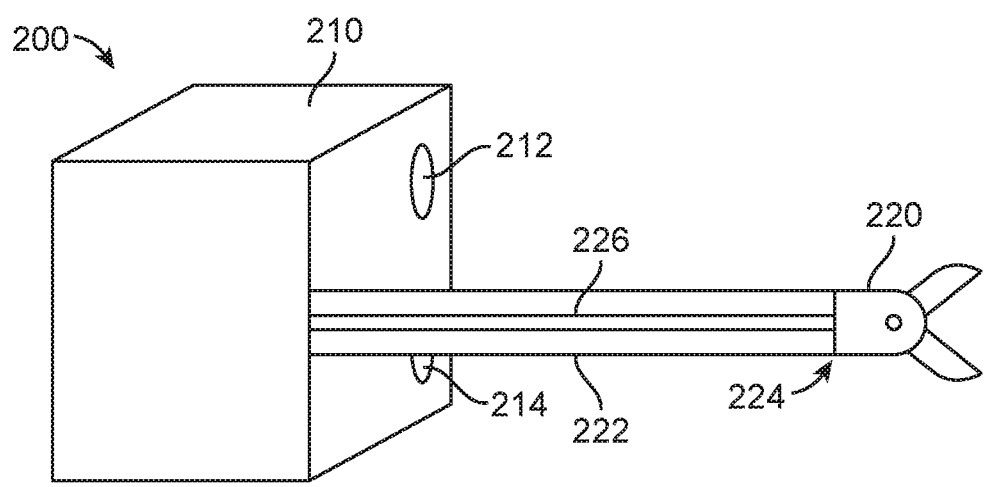
FIG. 2 is a perspective view of an exemplary embodiment of a surgical instrument including a force transmission mechanism.

FIG. 2 is a perspective view of an exemplary embodiment of a surgical instrument 200. As shown, the surgical instrument 200 includes a force transmission mechanism 210, an end effector 220 at a distal end 224 of the surgical instrument 200, and a shaft 222 connecting the force transmission mechanism 210 and the end effector 220. The surgical instrument 200 includes one or more members to translate force between the force transmission mechanism 210 and the end effector 220. For instance, one or more actuation member(s) 226 may connect the force transmission mechanism 210 to the end effector 220 to provide actuation forces to the end effector 220, such as by extending through an interior of the shaft 222. By utilizing actuation member(s) 226, the force transmission mechanism 210 actuates the end effector 220 to, for example, control a jaw of the end effector 220 (or other moveable part of the surgical instrument). Further, because the end effector 220 may be coupled to the shaft 222, force translated from the force transmission mechanism 210 to the end effector 220 may in turn be translated to the shaft 222, such as when force transmission mechanism 210 actuates end effector 220 in a rolling motion by rolling the shaft.

Actuation member(s) 226 may be in the form of tension elements, such as when the force transmission mechanism 210 is a pull-pull mechanism, or in the form of one or more force isolation rods, such as when force transmission mechanism 210 is a push-pull mechanism, such as a drive rod element, as described in U.S. Pat. No. 8,545,515, referenced above.

The force transmission mechanism 210 may include one or more components to engage with a patient side cart 100 to translate a force provided by the patient side cart 100 to the surgical instrument 200. According to an exemplary embodiment, the force transmission mechanism 210 may include one or more interface disks 212, 214 that engage with the PSM 120 of a patient side cart 100. Thus, interface disks 212, 214 may couple with drive mechanisms (e.g., servomechanisms) (not shown) in the PSM 120 and translate a force from the drive mechanisms (e.g., servomechanisms) to the surgical instrument 200. Thus, the interface disks 212, 214 utilize the actuation forces from the PSM 120 to actuate the instrument 200 through the force transmission mechanism 210 and actuation member(s) 226. For instance, in an exemplary embodiment, the first disk 212 may be configured to provide a rolling motion to the shaft 222 and provide a roll degree of freedom ("DOF") for the end effector 220, while the second disk 214 may operate other DOFs of the end effector 220, such as, for example, to open and close a jaw mechanism of the end effector.

Force transmission mechanisms, such as the force transmission mechanism 210 of FIG. 2, may be required to transmit relatively large forces between the PSM 120 and the end effector 220 or other movable component of the surgical instrument. For example, the end effector 220 may be in the form of opposing openable and closable jaws such as are used in forceps, grippers, and clamps for closing ligation clips (i.e., a clip applier), etc. Further, actuation of the end effector 220 may require a linear, translational movement of the member 226, e.g., when the member 226 is a drive rod, while the movement of the interface disks 212, 214 may be rotational movement. For these reasons, the force transmission mechanism 210 may be required to convert the input rotational movement of at least one of the interface disks 212, 214 to generally linear, translational movement of a drive rod to actuate the end effector 220. Thus, it is desirable to provide a force transmission mechanism capable of efficiently transmitting relatively large forces between the interface disks 212, 214 and the end effector 220, while at the same time converting rotary motion of an interface disk to translational motion of a drive rod.

Figure 6:
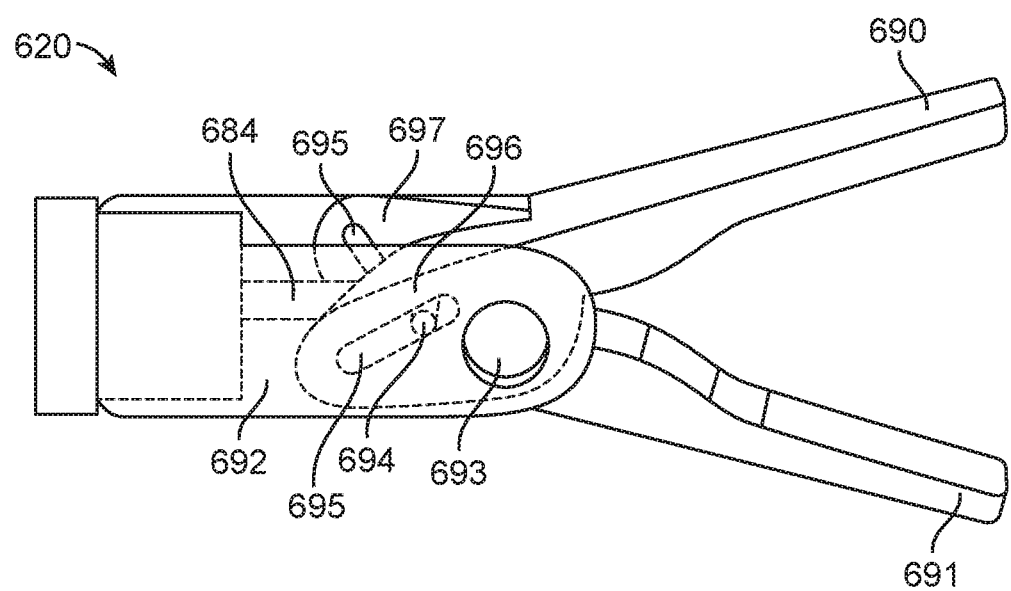
FIG. 6 is a perspective view of an exemplary embodiment of a surgical instrument end effector coupled with an actuation member.

Referring now to FIG. 6, an exemplary embodiment of an end effector 620 is shown. The end effector 620 may be or include any of the configurations discussed above, such as a clip applier, forceps, grippers, etc. The end effector 620 includes first and second jaws 690 and 691, respectively. The first and second jaws 690 and 691 are pivotally connected to a clevis 692 at a pivot, such as pinned joint 693. A distal end of a drive rod 684 includes, or is attached to, a pin 694 oriented orthogonally with respect to the drive rod 684. Stated another way, the drive rod 684 and pin 694 provide a T-shaped configuration at the distal end portion of the drive rod 684. Movement (e.g., translation) of the drive rod 684 in the proximal direction (e.g., actuated by force actuation mechanisms 210, 310, or 410, discussed in connection with FIGS. 2, 3, and 4 respectively) causes the pin 694 to travel within cam slots 695 formed in cam extensions 696, 697, respectively, of each of the jaws 690 and 691. Travel of the pin 694 in the proximal direction through the cam slots 695 causes the pin 694 to bear against the cam extensions 696, 697 within the slots 695, thereby move the jaws 690, 691 toward each other into a closed position. Movement (e.g., translation) of the drive rod 684 in the distal direction causes the pin 694 to bear against the cam extensions 696, 697 within the slots 695 to move the jaws 690, 691 away from each other and into an open position.

Accordingly, exemplary embodiments of force transmission mechanisms of the present disclosure may be configured to transmit force between an interface disk (e.g., interface disks 212, 214 of PSM 120) and an end effector 220 or other distal movable component of a surgical instrument. In some exemplary embodiments, the force transmission mechanisms according to the present disclosure also convert rotational motion of the interface disk to translational movement of an actuation member (e.g., a drive rod).

Figure 3:
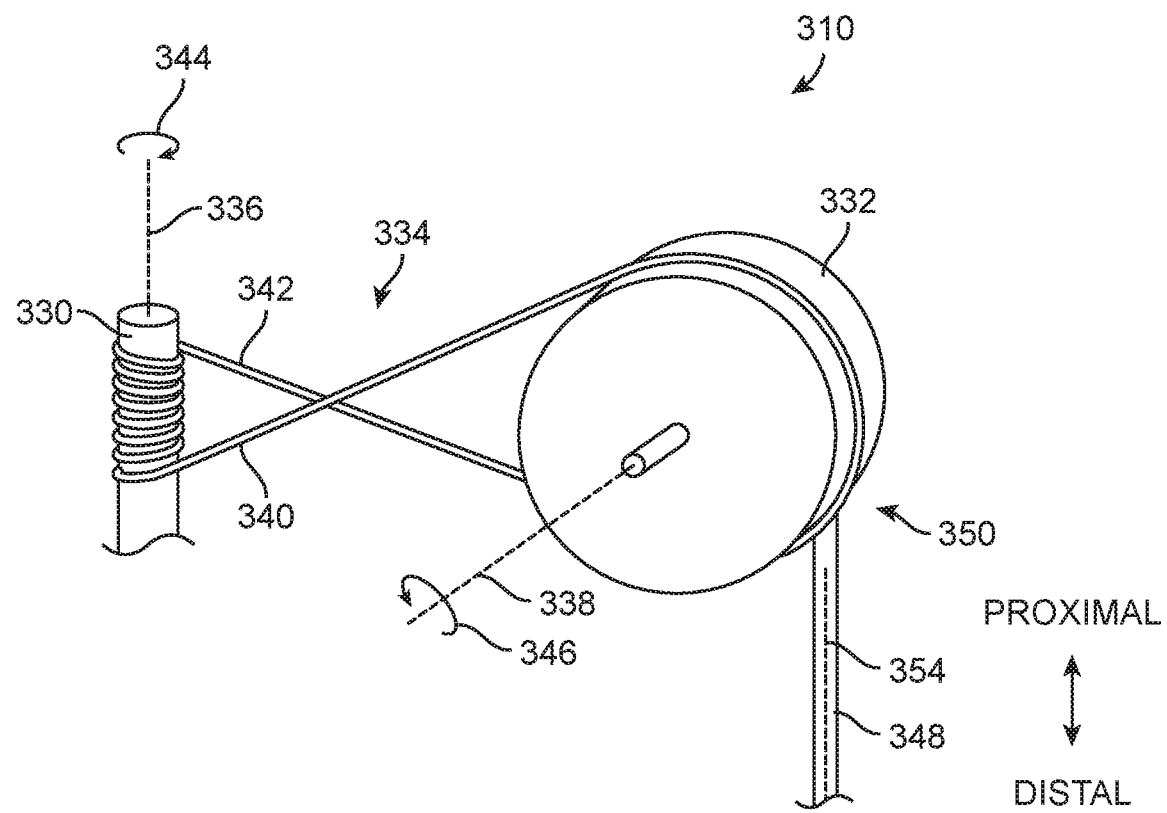
FIG. 3 is a schematic perspective view of an exemplary embodiment of a force transmission mechanism coupled with an actuation member (shown in partial view)
Figure 4:
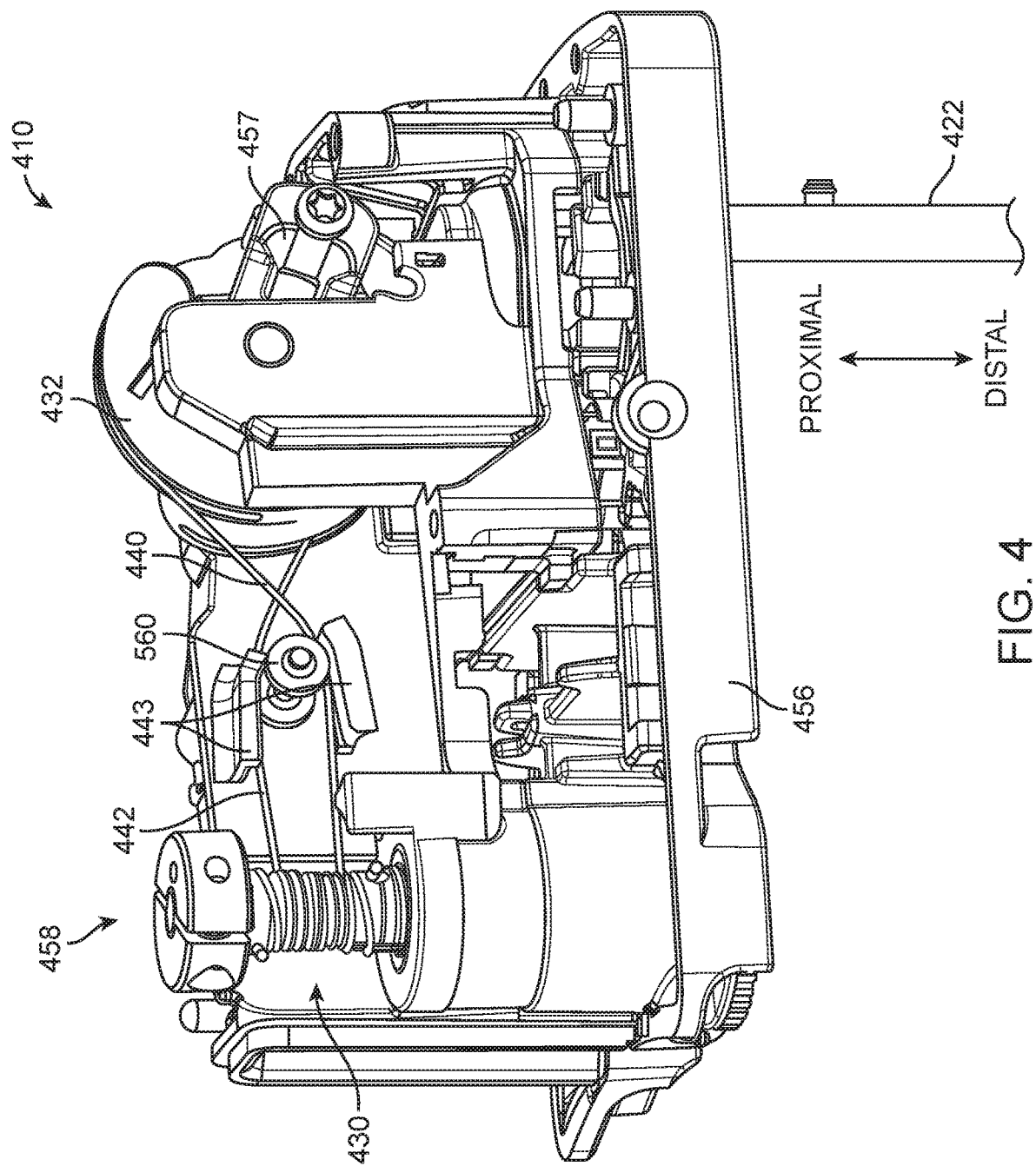
FIG. 4 is a perspective view of an exemplary embodiment of a force transmission mechanism and portion of a surgical instrument shaft.
Figure 5:
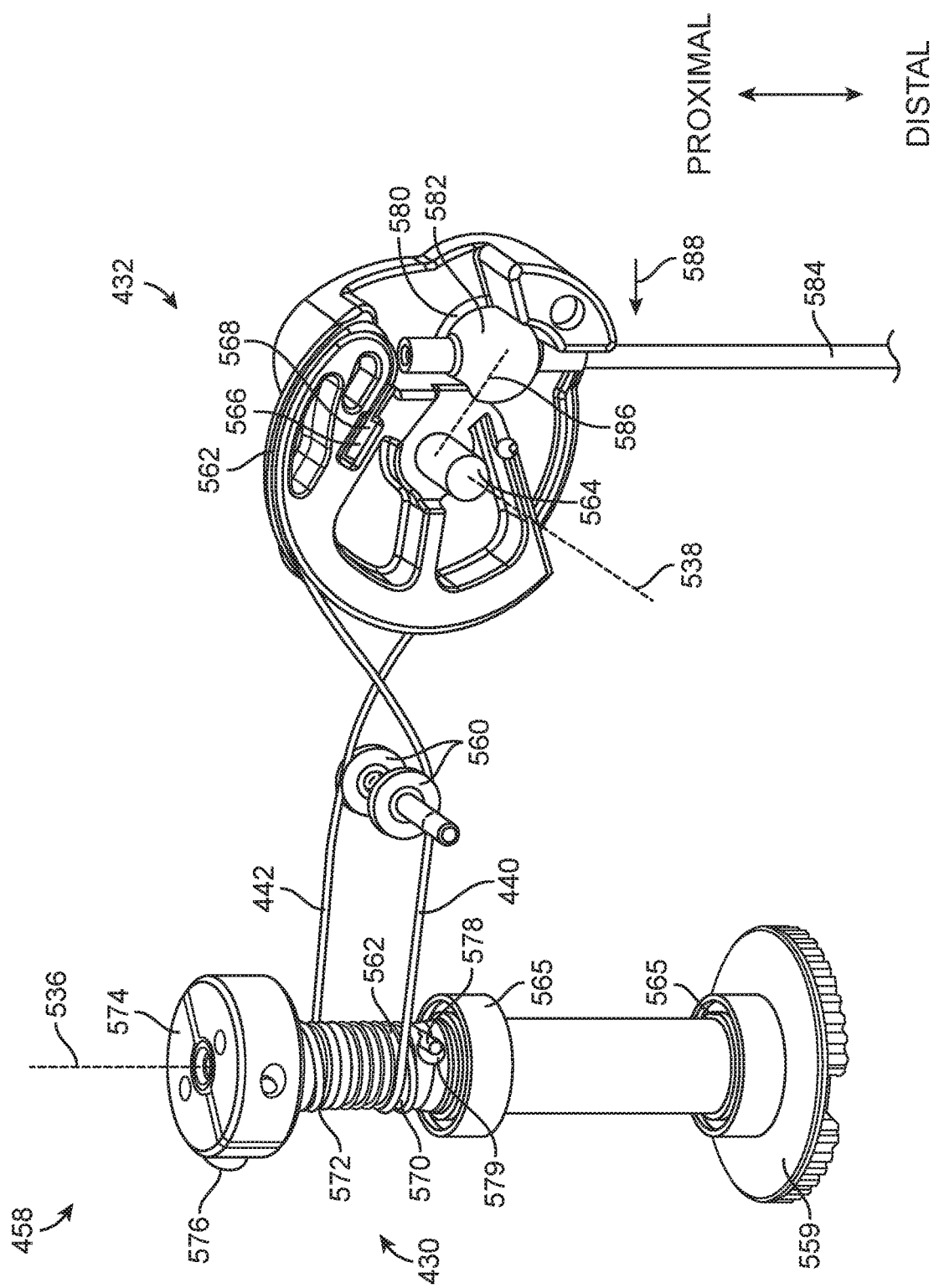
FIG. 5 is a perspective view of various mechanical components of the force transmission mechanism of FIG. 4 shown in isolation and coupled with an actuation member (shown in partial view)

Referring now to FIG. 3, a simplified, schematic diagram of a force transmission mechanism 310 illustrates exemplary components and mechanical operation of an exemplary embodiment of a force transmission mechanism. Other exemplary embodiments of force transmission mechanisms, such as the force transmission mechanism 410 described below in connection with FIGS. 4 and 5, may have similar mechanical functionality to the force transmission mechanism 310, as well as additional features and functionality. In the exemplary embodiment of FIG. 3, the force transmission mechanism 310 includes a drive pulley 330, which may form a portion of a drive pulley assembly 458 as shown in FIGS. 4 and 5, a driven pulley 332, and a drive cable 334 at least partially around each of the drive pulley 330 and the driven pulley 332. In some embodiments, the drive pulley 330 may be configured as a capstan. Rotational axes 336 and 338 of the drive pulley 330 and the driven pulley 332, respectively, may be oriented in a parallel or non-parallel relationship. In the exemplary embodiment of FIG. 3, the rotational axis 338 of the driven pulley 332 is oriented approximately perpendicular to the rotational axis 336 of the drive pulley 330 to impart movement to an actuation element rod 348 along a desired direction, as discussed below. In particular, in the orientation of FIG. 3 the drive pulley 330 has a vertical axis of rotation and the driven pulley 332 has a horizontal axis of rotation.

The drive cable 334 may be a single cable wrapped at least partially around the drive pulley 330 and then connected at ends to the driven pulley 332. Alternatively, the drive cable 334 may comprise two separate cables, each fixed at one end to the drive pulley 330 and at opposite ends to the driven pulley 332. Providing a drive cable 334 that has two separate cables may facilitate pre-tensioning of the drive cable 334, as described in more detail below. The drive cable 334 is wrapped around the drive pulley 330 such that a first portion 340 extends from the drive pulley 330 towards the driven pulley 332 and a second portion 342 extends from the drive pulley 330 also towards the driven pulley 332, but from a position on the drive pulley about diametrically opposite the first portion 340. As shown in FIG. 3, the drive cable 334 wraps multiple times around the drive pulley 330 such that the portions 340 and 342 extend from the drive pulley 330 at positions along the drive pulley that are separated by an axial distance. Respective ends of the first portion 340 and second portion 342 of the drive cable 334 are fixed to the driven pulley 332, and each portion 340 and 342 of the drive cable 334 wraps around at least a portion of the driven pulley 332. The drive cable 334 may be or include a single filament of material, or multiple filaments braided or twisted together. The drive cable 334 may comprise metal material such as stainless steel, a titanium alloy, tungsten, or other metals, or may comprise a polymer material or any other material having sufficient tensile strength and flexibility.

Rotation of the drive pulley 330 in direction 344 about the rotational axis 336 causes the first portion 340 to wind onto the drive pulley 330 and the second portion 342 to pay out (unwind) from the drive pulley 330. Tension generated in the first portion 340 imparts rotation of the driven pulley 332 about the driven pulley rotational axis 338 in direction 346. As this occurs, the second portion 342 pays out from the drive pulley 330 and winds onto the driven pulley 332.

Conversely, when the drive pulley 330 is rotated opposite the direction 344 about the rotational axis 336, the second portion 342 of the drive cable 334 is wound onto the drive pulley 330, and the first portion 340 pays out from the drive pulley 330. Tension in the second portion 342 of the drive cable 334 imparts rotation of the driven pulley 332 in a direction opposite direction 346, causing the first portion 340 to be wound onto the driven pulley 332 while the second portion 342 pays out from the driven pulley 332. In this manner, rotational motion of the drive pulley 330 is transmitted via the drive cable 334 to the driven pulley 332. Depending on the relative sizes of the drive pulley 330 and driven pulley 332, and how the drive cable 334 is wrapped around each, a torque conversion may occur from the rotary input at the drive pulley 330 to the rotary output at the driven pulley 332.

The driven pulley 332 may be operably coupled to a proximal end 350 of an actuation element, such as a push-pull rod 348, a distal end (not shown in FIG. 3) of which is operably coupled with and configured to actuate a distal component of the surgical instrument, such as an end effector, e.g., end effector 220 (FIG. 2) or end effector 620 (FIG. 6). As shown in FIG. 3, the actuation rod 348 can be coupled to the driven pulley 332 with, e.g., a joint such as a ball joint (not shown). Rotation of the driven pulley 332 about the rotational axis 338 causes translational movement of the rod 348 along longitudinal axis 354 along a proximal-distal direction, as the rotating driven pulley 332 applies a force to the rod 348 through the ball joint 352. Translation of the actuation rod 348 actuates the end effector 220 (FIG. 2) or 620 (FIG. 6), as discussed herein in connection with FIGS. 2 and 6.

FIG. 4 shows an exemplary embodiment of a portion of a force transmission mechanism 410. The embodiment shown in FIG. 4 may have functionality similar to that previously described and shown in FIG. 3, with specific features and aspects in addition to those discussed in connection with FIG. 3. For example, the force transmission mechanism 410 may include a chassis 456 to which various components of the force transmission mechanism 410 are attached. While the chassis 456 is shown in FIG. 4 with mechanical components of the force transmission mechanism 410 exposed for clarity, the chassis 456 may further include a cover (not shown) configured to engage with the depicted chassis to enclose and protect the mechanical components of the force transmission mechanism 410 from foreign objects, contamination, etc. during use. The chassis 456 may be configured to be attached to a PSM 120 (FIG. 1), and may include interface disks (not shown) such as interface disks 212, 214 (FIG. 2) configured to interact with mechanisms of the PSM 120.

An instrument shaft 422 is coupled to the chassis 456 at a proximal end of the instrument shaft 422. A distal end (not shown) of the instrument shaft 422 includes an end effector, such as end effector 220 shown in FIG. 2. The instrument shaft 422 may be configured to be rotatable relative to the housing portion 456, e.g., based on a rotational input to an interface disk, such as one of the interface disks 212, 214 (FIG. 2). An actuation element, such as push-pull rod 348 (FIG. 3), extends at least partially through the instrument shaft 422 and is configured to actuate the end effector positioned at the distal end of instrument shaft 422, or another component of the instrument shaft 422. The rod may actuate the end effector as it translates in the proximal-distal direction described above in connection with FIGS. 2 and 6.

The force transmission mechanism 410 includes a drive pulley assembly 458 comprising a drive pulley (capstan) 430 rotationally coupled with the chassis 456. A first drive cable 440 and a second drive cable 442 are fixed at respective first ends to the drive pulley 430. The first and second drive cables 440, 442 are fixed at respective second ends to the drive pulley 430 and fixed at respective second ends to a driven pulley 432. Rotation of the drive pulley 430 results in corresponding rotation of the driven pulley 432 in a manner similar to that described above in connection with FIG. 3. Cable guides (e.g., fenders) 443 ensure that the first and second actuator cables 440, 442 do not derail from idler pulleys 560, which are discussed further below in connection with FIG. 5. The drive rod 348 is coupled with the driven pulley 432 with a ball joint (not shown), discussed below in connection with FIG. 5. A retainer element 457 may retain the actuation member drive rod 348 of FIG. 3 to the driven pulley 432.

Referring now to FIG. 5, mechanical components of the force transmission mechanism 410 are shown without the housing 456 shown in FIG. 4 to simplify illustration of the various mechanical components. The drive pulley assembly 458 may include or be coupled with a drive input disk 559, which may be meshed with a drive output disk (not shown) or otherwise rotationally coupled with one or more interface disks (such as interface disks 212, 214 shown in FIG. 2) actuated by the PSM 120 (FIG. 1) to rotate the drive pulley assembly 458.

The force transmission mechanism may include components configured to route the first and second actuator cables 440, 442 between the drive pulley 430 and the driven pulley 432 and ensure that the actuator cables 440, 442 wind on and off the drive pulley 430 and driven pulley 432 correctly. For example, the force transmission mechanism may include idler pulleys 560 about which the first and second actuator cables 440, 442 are directed. As shown, for example, cable 442 extends over one idler pulley 560 and cable 440 extends under the other idler pulley 560. The idler pulleys 560 may be positioned to ensure the first and second actuator cables 440, 442 extend from the drive pulley 430 at angles substantially perpendicular to the rotational axis 536 of the drive pulley 430. Similarly, the idler pulleys 560 may be positioned to ensure the first and second actuator cables 440, 442 extend from the driven pulley 432 at angles substantially perpendicular to the rotational axis 538 of the driven pulley 432. Such an arrangement may increase (e.g., maximize) the force transmission capability of the force transmission mechanism 410 by providing an optimal geometric relationship between the actuator cables 440, 442 and the drive and driven pulleys 430, 432. Such a geometric relationship may reduce (e.g., minimize) loss. While the exemplary embodiment of FIG. 5 includes idler pulleys 560, other components such as guides, pins, or any other routing device may be used to align the actuator cables 440, 442 with the drive pulley 430 and driven pulley 432 to optimize force transmission between the drive and driven pulleys 430, 432.

The drive pulley 430 and the driven pulley 432 may include grooves 562, 563 in which the actuator cables 440, 442 are seated to ensure the actuator cables 440, 442 remain routed correctly around the respective outer diameters of the drive pulley 430 and driven pulley 432. The driven pulley 432 may be rotationally coupled with the chassis 456 (FIG. 4) with a pin 564. The pin 564 may be supported directly by the chassis 456, or may rotate on plain bearings, ball bearings, roller bearings, etc. disposed within the housing 456. The drive pulley assembly 458 may be mounted within bearings 565 disposed within the housing 456 (FIG. 4).

The first and second actuator cables 440, 442 may be fixed to the driven pulley 432 by first crimping, soldering, or otherwise affixing enlarged ends (only enlarged end 566 of the first actuator cable 440 shown in FIG. 5 due to perspective of the drawing) to ends of the first and second actuator cables 440, 442, and pressing the respective enlarged ends into recesses 568 within the driven pulley 432. The first and second actuator cables 440, 442 are partially wrapped around the grooves 562 of the driven pulley 432 and routed over the idler pulleys 560 as described above.

According to an exemplary embodiment, the drive pulley assembly 458 may include features configured to enable pre-tensioning of the first and second actuator cables 440, 442 during assembly of the force transmission mechanism. For example, in the exemplary embodiment of FIG. 5, the drive pulley 430 includes a lower sheave 570 and an upper sheave 572. The lower sheave 570 and upper sheave 572 are configured to rotate independently during a pre-tensioning operation (e.g., during assembly of the force transmission mechanism 410), and to rotate together during operation of the force transmission mechanism. To achieve this, the upper sheave 572 includes a split collar 574 with a clamp screw 576 that can be tightened to rotationally lock the upper sheave 572 with the lower sheave 570. The first actuator cable 440 may include an enlarged end, such as barrel end 578, that can be crimped, soldered, welded, or otherwise fastened to an end of the first actuator cable 440. The barrel end 578 may be inserted within a recess 579 of the lower sheave 570, such that rotation of the lower sheave 570 winds a portion of the first actuator cable 440 around the lower sheave 570. The driven pulley 432 may be held in place while a torque is applied to the lower sheave 570 to generate a tension in the first actuator cable 440. A similar enlarged end of the second actuator cable 442 (not shown due to the perspective of FIG. 5) may be inserted within a similar recess (also not shown) of the upper sheave 572, and the second actuator cable 442 can be wound and pre-tensioned by rotating the upper sheave 572 in the opposite rotational direction relative to the pre-tensioning torque applied to the lower sheave 570. The clamp screw 576 is then tightened, rotationally locking the lower sheave 570 and the upper sheave 572 together and maintaining the tension in both the first and second actuator cables 440, 442.

In an exemplary embodiment, the driven pulley 432 includes a socket 580 configured to accept a ball joint 582. The ball joint 582 connects to the actuation (drive) rod 584 operably connected to an end effector (e.g., end effector 220 shown in FIG. 2 or end effector 620 shown in FIG. 6). The ball joint 582 and the drive rod 584 may be free to rotate about a longitudinal axis of the rod 584 within the ball socket 580. For example, the instrument shaft 422 (FIG. 4)

may be configured to rotate along a longitudinal axis thereof in response to an input from one or more interface disks, such as interface disks 212, 214 (FIG. 2). An end effector (e.g., end effector 220 or end effector 620) may be coupled to the end of the instrument shaft 422 and operably coupled with the drive rod 584, e.g., such that translation of the drive rod 584 actuates the end effector as described above. The drive rod 584, the instrument shaft 422, and the end effector may rotate in unison based on an input from an interface disk. As the instrument shaft 422, end effector, and drive rod 584 rotate, the ball joint 582 rotates within the ball socket 580. Such a ball joint arrangement, and methods and devices for fastening the ball joint to the drive rod, are described in U.S. Patent App. Pub. No. US 2014/0338477 A1 (filed May 13, 2014), the entire disclosure of which is incorporated by reference herein.

The drive pulley 430 and the driven pulley 432 may be configured to provide a mechanical advantage between the input to the drive pulley assembly 458 (e.g., an input torque applied by a disk interface to the drive pulley assembly 458 to actuate the force transmission mechanism) and the output to the end effector (e.g., end effector 220 (FIG. 2) or 620 (FIG. 6)). For example, a diameter of the drive pulley 430, a diameter of the driven pulley 432, and a distance of the ball join 582 from the rotational axis of the driven pulley 432, may together define a mechanical advantage to deliver a force sufficient to actuate the end effector. For example, in an embodiment in which the end effector is a jaw mechanism configured to apply ligation clips, e.g., to blood vessels of a patient, (e.g., the end effector comprises a "clip applier"), the end effector may require a force of up to approximately 45 pounds (45 lbf; 200 N) to be delivered by the actuation rod 584, for example to close the jaws as described above with reference to the exemplary embodiment of FIG. 6. The drive pulley 430 and the driven pulley 432 may have different diameters to provide a desired mechanical advantage between an input to the drive pulley assembly 458 and an output of the driven pulley 432. For example, a tensile force applied to the first or second drive cables 440, 442 by rotation of the drive pulley assembly 458 may deliver a force at the actuation rod 584 equal to the tensile force applied to the cables multiplied by a factor greater than one. In an exemplary embodiment, the drive pulley assembly 458 is configured to apply a nominal tensile force of about 30 lbf to the first or second actuator cable 440, 442 as each cable is wound around the drive pulley assembly 458, and the mechanical advantage factor may be equal to about 1.5, thereby delivering about 45 lbf/200 N to the actuation rod 584 to actuate the end effector. Other forces and factors of mechanical advantage as required by the specific application, type of end effector, etc. are within the scope of the disclosure, and the mechanical advantage may be tailored to the specific application by varying the relative size of the diameters of the drive pulley 430 and driven pulley 432 and the distance from the rotational axis of the driven pulley 432 to the ball joint 582.

In addition, the mechanical advantage provided by the force transmission mechanism 410 may vary depending on the rotational position of the driven pulley 432. For example, the mechanical advantage may be greatest when the ball joint 582 is horizontally aligned (in the orientation view of FIG. 5) with the rotational axis 538 of the driven pulley 432, as the length of an effective lever arm 586 acting on the ball joint 582 is at a maximum. Stated another way, the lever arm 586 is at a maximum effective length when the lever arm 586 is orthogonal to both the rotational axis 538 of the driven pulley 432 and the longitudinal axis of the drive rod 584. As rotation of the driven pulley 432 moves the ball joint 582 away from the position of maximum effective length, a maximum force delivered to the end effector is reduced.

Accordingly, in exemplary embodiments, the rotational position of the driven pulley 432 and the ball joint 582 may be optimized such that the mechanical advantage delivered by the force transmission mechanism 410 is at a maximum when the end effector or other actuated component of the surgical instrument is in a position requiring the maximum applied force. For example, in embodiments in which the end effector comprises a jaw mechanism configured as a clip applier (see, e.g., FIG. 6), the required force may be greatest when the jaws of the end effector approach a closed position. Consequently, the force transmission mechanism may be configured such the lever arm 586 approaches the maximum effective length when the jaws of the end effector approach a closed position. In other exemplary embodiments, such as embodiments in which the end effector is configured as forceps, grippers, or other tools, the position in which the lever arm 586 is at the maximum effective length may or may not correspond to a closed position of the jaws of the end effector. For example, in an exemplary embodiment in which the end effector 220, 620 comprises a dissecting instrument, the rotational position of the driven pulley 432 and the ball joint 582 may be selected such that the mechanical advantage delivered by the force transmission mechanism 410 provides maximum force to open the jaws from a closed position. As an additional non-limiting example, with some end effector tools, such as bipolar cautery forceps, a possibility exists that tissue may stick to grippers of the tool, and thus require relatively high forces to open the tool. In such applications, the mechanical advantage may be maximized for the force available to open the tool over the force to close the tool, and the drive rod 584 and ball joint 582 may be configured accordingly. Likewise, those of ordinary skill in the art would appreciate that force transmission mechanisms may be configured to transmit maximum force over other ranges of motions when used to actuate other actuatable surgical instrument components, such as for example, articulatable wrist mechanisms, etc.

In exemplary embodiments, the actuation rod 584 may comprise a resilient material configured to deform elastically in a transverse direction 588 as the driven pulley 432 rotates. For example, in addition to translational movement along the longitudinal axis of the actuation rod 584, the ball joint 582 and the rod 584 near the ball joint 582 may be displaced along an arc as the driven pulley 432 rotates, the ball joint 582 being constrained by ball socket 580 to a circular movement. Stated another way, as the driven pulley 432 rotates clockwise as viewed in FIG. 5, the ball joint 582 may move downward and slightly toward the drive pulley assembly 458. However, the radius of the arc may be relatively large compared to the translational distance of the ball joint and rod along the longitudinal axis of the rod 584, and some elastic deformation of the rod 584 may permit movement of the ball joint 582 along the arc as the rod 584 translates. Suitable materials for the drive rod 584 may include relatively elastic materials such as stainless steel, titanium, nitinol, or other metal alloys, polymer materials, or other materials.

The force transmission mechanisms disclosed herein may be desirable over other configurations. For example, compared to various toothed gear arrangements (e.g., helical gear and rack assembly), exemplary embodiments of the disclosure exhibit lower friction and thus higher force transmission efficiency. For example, in some situations intermeshing toothed gear arrangements may exhibit 50 percent or less force transmission efficiency, due to frictional losses and losses attributable to non-optimal geometry of the gear mating surfaces. Embodiments of the disclosure can exhibit force transmission efficiencies above 50 percent, above 75 percent, etc. Additionally, embodiments of the disclosure can exhibit a range of motion of the actuation rod 584 greater than a range of motion obtainable with a helical gear and rack configured to fit within a similar enclosure. Finally, under high applied torque, helical gears and components supporting and positioning the helical gears may deflect, allowing the intermeshing teeth of components (and actuation member) to momentarily disengage and "skip" teeth, leading to misalignment of the mechanism, damage to gear teeth and other components, etc. Thus, embodiments of the disclosure may promote the reliability and functionality of the force transmission mechanism, while permitting an overall compact size to be implemented.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the inventions disclosed herein. It is intended that the specification and examples be considered as exemplary only, with the following claims being provided their full scope of breadth, including equivalents, under the applicable law.

What is claimed is:

1. A force transmission mechanism for an instrument, comprising:
    a drive pulley rotatable about a first rotational axis;
    one or more drive cables operably coupled with the drive pulley;
    a driven pulley operably coupled with the or each of the one or more drive cables, the driven pulley rotatable about a second rotational axis oriented in a non-parallel relationship to the first rotational axis; and
    a push/pull actuation member engaged with the driven pulley, the push/pull actuation member being configured to transmit compressive and tensile forces along a shaft of the instrument to actuate an end effector of the instrument;
    wherein rotational motion of the driven pulley causes translational movement of the push/pull actuation member to actuate the end effector.

2. The force transmission mechanism of claim 1, wherein the first rotational axis and the second rotational axis are orthogonal to one another.

3. The force transmission mechanism of claim 1, wherein:
    the force transmission mechanism comprises an idler pulley engaged with a drive cable of the one or more drive cables; and
    the idler pulley is positioned between the drive pulley and the driven pulley.

4. The force transmission mechanism of claim 1, wherein:
the one or more drive cables comprise a first drive cable portion and a second drive cable portion;
the force transmission mechanism comprises a first idler pulley engaged with the first drive cable portion between the drive pulley and the driven pulley; and
the force transmission mechanism comprises a second idler pulley engaged with the second drive cable portion between the drive pulley and the driven pulley.

5. The force transmission mechanism of claim 1, wherein the force transmission mechanism is configured to provide a mechanical advantage ratio between a tensile force in the one or more drive cables and an actuation force applied by the push/pull actuation member to the end effector.

6. The force transmission mechanism of claim 5, wherein the mechanical advantage ratio ranges from 1:1 to 3:1.

7. The force transmission mechanism of claim 6, wherein the mechanical advantage ratio is 1.5:1.

8. The force transmission mechanism of claim 1, further comprising a ball joint coupling the push/pull actuation member to the driven pulley.

9. The force transmission mechanism of claim 8, wherein:
the ball joint comprises a ball element and a socket configured to receive the ball element;
the driven pulley comprises the socket;
the ball element is rotatably received by the socket; and
the push/pull actuation member extends from the ball element.

10. A force transmission mechanism for an instrument, the force transmission mechanism comprising:
a drive pulley;
a driven pulley;
a first drive cable portion operably coupled to the drive pulley and the driven pulley;
a second drive cable portion operably coupled to the drive pulley and the driven pulley; and
a push/pull actuation member engaged with the driven pulley, the push/pull actuation member being configured to transmit compressive and tensile forces along a shaft of the instrument to actuate an end effector of the instrument; wherein:
the first drive cable portion is wrapped at least partially around the drive pulley in a first direction;
the second drive cable portion is wrapped at least partially around the drive pulley in a second direction opposite the first direction; and
the first drive cable portion and the second drive cable portion extend from the drive pulley toward the driven pulley in the same direction at diametrically opposite positions of the drive pulley; and
rotational motion of the driven pulley causes translational movement of the push/pull actuation member to actuate the end effector.

11. The force transmission mechanism of claim 10, wherein:
the driven pulley comprises an outer diameter; and
the push/pull actuation member is engaged with the driven pulley at a location of the driven pulley within the outer diameter.

12. The force transmission mechanism of claim 10, wherein the first drive cable portion and the second drive cable portion are separate cables.

13. The force transmission mechanism of claim 10, wherein the first drive cable portion and the second drive cable portion each have an end secured to the driven pulley.

14. An instrument comprising:
a shaft;
an end effector at a distal portion of the shaft; and
a force transmission mechanism at a proximal portion of the shaft, the force transmission mechanism comprising:
a drive pulley rotatable about a first rotational axis,
a drive cable operably coupled with the drive pulley,
a driven pulley operably coupled with the drive cable and rotatable about a second rotational axis oriented in a non-parallel relationship with the first rotational axis, and
a push/pull actuation member engaged with the driven pulley and to the end effector;
wherein the push/pull actuation member extends along the shaft and is configured to transmit compressive and tensile forces to actuate the end effector; and
wherein rotational motion of the driven pulley causes translational movement of the push/pull actuation member to actuate the end effector.

15. The instrument of claim 14, wherein:
the end effector comprises jaws moveable between a closed position and an open position;
an effective distance between a ball element and the second rotational axis of the driven pulley is at a maximum when the jaws of the end effector are in the closed position; and
the push/pull actuation member extends from the ball element.

16. The instrument of claim 14, wherein the end effector comprises a ligation clip applier tool.

17. The instrument of claim 14, wherein the end effector comprises forceps.

18. The instrument of claim 14, wherein:
the instrument further comprises an input device operably coupled to the drive pulley; and
the input device is configured to transmit a rotational input of a drive mechanism of a patient side manipulator to the drive pulley.

19. The instrument of claim 14, wherein:
the drive cable comprises a first end portion and a second end portion; and
the first end portion and the second end portion are secured to the driven pulley.

20. An instrument, comprising:
a drive pulley;
a driven pulley;
a first drive cable portion wrapped in a first direction around the drive pulley, extending to the driven pulley, and wrapped in a second direction around the driven pulley;
a second drive cable portion wrapped in a third direction around the drive pulley, extending to the driven pulley, and wrapped in a fourth direction around the driven pulley, the third direction being opposite the first direction, and the fourth direction being opposite the second direction; and
an actuation member having a first end and a second end opposite the first end, the first end being pivotally coupled to the driven pulley, and the second end being engaged with a movable component at a distal end of the instrument.

21. The instrument of claim 20, wherein a rotational axis of the drive pulley and a rotational axis of the driven pulley are perpendicular.

* * * * *